United States Patent [19]

Madrange et al.

[11] 4,366,827

[45] Jan. 4, 1983

[54] PROCEDURE FOR THE PERMANENT RESHAPING OF HAIR, AND COMPOSITION INTENDED FOR CARRYING OUT SAID PROCEDURE

[75] Inventors: Annie Madrange, Saint Germain en Laye; Daniel Boixader, Bry sur/Marne, both of France

[73] Assignee: Societe Anonyme dite: L'Oreal, Paris, France

[21] Appl. No.: 217,694

[22] Filed: Dec. 18, 1980

[30] Foreign Application Priority Data

Dec. 28, 1979 [FR] France .................................. 79 32078
Dec. 12, 1980 [FR] France .................................. 80 26421

[51] Int. Cl.$^3$ ............................................. A45D 7/00
[52] U.S. Cl. ......................................... 132/7; 424/71; 424/DIG. 2
[58] Field of Search ......... 132/7; 424/DIG. 2, 71–72; 525/329, 330, 336, 229, 264

[56] References Cited

U.S. PATENT DOCUMENTS

| | | | |
|---|---|---|---|
| 3,964,499 | 6/1976 | Wajaroff | 132/7 |
| 4,134,411 | 1/1979 | Yamazaki | 132/7 |
| 4,197,865 | 4/1980 | Jacquet | 424/DIG. 2 |

*Primary Examiner*—G. E. McNeil
*Attorney, Agent, or Firm*—Cushman, Darby & Cushman

[57] ABSTRACT

A process for the permanent reshaping of hair consists in reducing the bisulfide bonds of the keratin by applying a reducing composition containing a cationic polymer and reforming the said bonds by applying an oxidizing composition in the presence of an anionic surface active agent.

14 Claims, No Drawings

PROCEDURE FOR THE PERMANENT RESHAPING OF HAIR, AND COMPOSITION INTENDED FOR CARRYING OUT SAID PROCEDURE

The subject of the present invention is an improvement perfecting the procedure for the permanent reshaping of hair, and a composition designed for carring out said procedure.

It is known that the conventional technique for permanently reshaping hair consists of a first step to open the bisulfide bonds of the keratin with the help of a composition containing a reducing agent (reduction stage) followed, preferably after rinsing of the hair, by a second step reconstituting said bonds by applying an oxidizing composition to the hair which is held under tension (oxidation stage, also known as fixation), this so as to give the desired shape to the hair. It is also known that this technique makes possible either the waving of the hair or the straightening or uncrimping of the hair.

The reducing and oxidizing compositions are well known and have been described in most works on cosmetology, inter alia in the book by E. SIDI and C. ZVIAK, *Problemes capillaires* (Capillary problems), Gauthier Villard: Paris, 1966.

In addition to the reducing agent, the compositions for the first step of a permanent contain adjuvants which make it possible for them to take the form of lotions, creams, gels or powders to be diluted in a liquid base.

In the compositions for the first step, the reducing agent is preferably a mercaptan, and in the compositions for the second step, the oxidizing agent is preferably oxygenated water or an alkaline bromate.

It is widely known that the procedures which make it possible to reshape hair permanently have the effect of weakening the hair and harming its general appearance.

The present invention constitutes an improvement perfecting the procedure for the permanent reshaping of the hair as referred to above which makes it possible to give the hair more softness to the touch, improved characteristics for combing and brushing, and better esthetic appearance.

More specifically, the subject of the present invention is a procedure for the permanent reshaping of the hair consisting in a first step during which the bisulfide bonds of the keratin are reduced by the application of a reducing compound, and then a second step during which the said bonds are reformed by the application of an oxidizing compound, said procedure being characterized essentially by the fact that the reduction stage is carried out with the help of a reducing composition containing at least one cationic polymer and by the fact that the fixing stage is carried out in the presence of at least one tensio-active anionic agent.

The hair to which the treatment for permanent reshaping is applied must of course be subjected, in a known manner, to tension making it possible to reform the keratin bonds of the hair while the latter is in the new desired shape. In the case of a wave, the new shape is obtained by using rollers or curlers. In the case of straightening, the new shape is obtained, for example, by smoothing the hair.

In the procedure according to the invention, it is desirable for the cationic polymer to be stable in a reducing, alkaline medium, but separate conditioning is conceivable. Likewise, the tensio-active anionic agent is preferably stable in an oxidizing medium; in certain cases it is preferable to prepare the oxidizing composition at the time it is to be used.

In cases where the procedure according to the invention is a procedure for waving the hair, the reducing composition is applied to wet hair which has previously been rolled on rollers with a diameter ranging from 4 mm to 20 mm, or the composition is applied as the rolling proceeds; it is allowed to act for 5 to 60 minutes, in particular for 5 to 30 minutes, and then rinsed thoroughly, after which the oxidizing composition containing the tensio-active anionic agent is applied to the rolled hair.

After allowing the said composition to act for a period of from 2 to 10 minutes, the rollers are removed, the hair is rinsed thoroughly and then dried.

In cases where a straightening or uncrimping of the hair is desired, the mechanical deformation of the hair making it possible to fix it in its new shape is generally obtained by an operation involving the smoothing of the hair after application of the reducing compound, doing so with a large-toothed comb, with the back of a comb, or with the hand. After a setting time of 5 to 60 minutes, in particular from 5 to 30 minutes, there is generally a new smothing in which excessive pulling on the hair is avoided, followed by a careful rinsing and the application of the oxidizing or fixing compound, which is allowed to act for about 2 to 10 minutes. The hair is then carefully rinsed.

According to a variant of the procedure according to the invention, the so-called oxidation or fixing stage may be carried out in two steps, i.e., by first applying an oxidizing composition and then by applying a composition containing the tensio-active anionic agent to the hair (under or not under tension).

Indeed, it has been observed that excellent results can also be obtained by breaking down the second step.

According to the procedure used in the invention, the reducing composition is of the same type as those conventionally used in permanents, i.e., preferably a solution containing at least one reducing agent such as, for example, a mercaptan, an ammonium or alcalin bisulphite or sulphite, said composition generally having a pH in the range of 6.5 to 10.

Preferably, the reducing agent is present in the composition in a concentration of 2 to 25 percent by weight with respect to the total weight of the reducing composition. This reducing agent, which is a reducing agent customarily used in operations for permanently reshaping the hair, may for example be thioglycolic acid or thiolactic acid or a mixture of the two; in this case the concentration of these reducing agents generally ranges from 2 to 11 percent by weight.

The reducing agent may also be an alkalin or ammonium bisulfite or sulfite; in this case the concentration generally ranges from 2 to 15 percent. The reducing agent may also be an ester of thioglycolic acid or thiolactic acid (for example monothioglycolate of glycerol or glycol) in a concentration ranging, for example, from 5 to 25 percent by weight.

The reducing agent may also be cystein or one of its derivatives, for example its salts such as the hydrochlorate.

The pH of the reducing compositions is generally obtained with the help of alkalin agents such as, for example, ammonia, monoethanolamine, diethanolamine, triethanolamine, or an alkaline or ammonium carbonate or bicarbonate.

The reducing compounds for carrying out the procedure according to the invention may likewise be of the exothermic variety, i.e., those which induce a certain amount of heating when applied to the hair, which may be perceived as somewhat pleasant by the person to whom the first step of the permanent or straightening is being applied.

The cationic polymer is generally present in the reducing compositions in a concentration ranging from 0.2 to 5 percent by weight with respect to the total weight of the composition.

The term "cationic polymer" is used to indicate the polycationic polymers of which a sizable proportion of the bond patterns feature, either in the chain or in a lateral substitute, tertiary amine or quaternary ammonium groups.

Among the cationic polymers, those preferred for use in accordance with the invention are selected from among:

(A) the water-soluble cyclopolymers with a molecular weight of from 2,000 to 3,000,000 with, as principal component of the chain, units corresponding to formula (Ia) or (Ib) below:

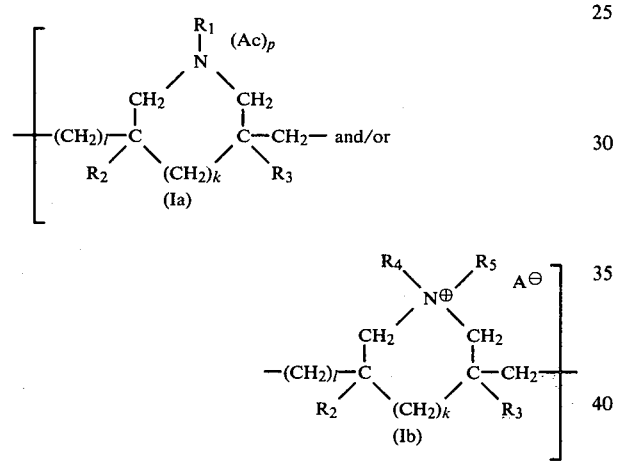

in which:
k is 0 or 1
  if k=0 l=1
  if k=1 l=0
p=0 or 1
$R_2$ and $R_3$, whether identical or different, represent an atom of hydrogen or a methyl radical,
$R_1$ represents a radical taken from the group made up of:
  (i) an alkyl radical with from 1 to 22 carbon atoms,
  (ii) a hydroxyalkyl radical with from 1 to 5 carbon atoms,
  (iii) an amidoalkyl radical with from 1 to 5 carbon atoms,
  (iv) —$CH_2$—$COOR_6$, $R_6$ representing an alkyl radical with from 1 to 3 carbon atoms,

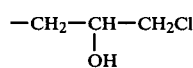  (v)

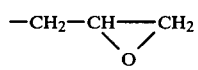  (vi)

(vii) —$(CH_2)_n$—CN, where n is equal to 1 or 2, (viii) —$COR_7$, with $R_7$ representing an alkyl radical with from 1 to 3 carbon atoms, a —$CCl_3$ radical, a —$CH_2Cl$ radical, a phenyl radical or a radical with the formula:

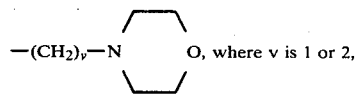

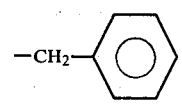 (ix)

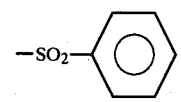 (x)

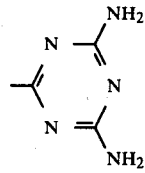 (xi)

$R_4$ represents an atom of hydrogen or a radical from the group made up of:
  (a) —$(CH_2)_m$—$CH_3$, where m is from 0 to 21 inclusive,
  (b) a hydroxyalkyl radical with 1 to 5 carbon atoms,
  (c) an amidoalkyl radical with from 1 to 5 carbon atoms,
  (d) —$(CH_2)_q$—$OC_2H_5$, where q is 1 or 2,
  (e) —$CH_2COOR_6$, with $R_6$ meaning the same as above,
and

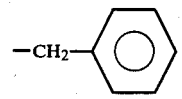 (f)

$R_5$ represents a radical taken from the group made up of:
  (1) —$(CH_2)_m$—$CH_3$, with m having the same meaning as above,
  (2) a hydroxyalkyl radical with from 1 to 5 carbon atoms,
  (3) an amidoalkyl radical with from 1 to 5 carbon atoms,
  (4) —$(CH_2)_q$—$OC_2H_5$, where q is 1 or 2,
  (5) —$CH_2$—$COOR_6$, $R_6$ having the same meaning as above,

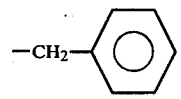 (6)

(9) —$(CH_2)_n$—CN, where n is equal to 1 or 2,
  (10) —$COR_7$, where $R_7$ has the same meaning as above,

(11) 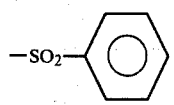

(12) 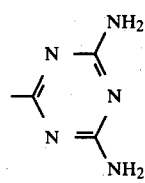

(13) —CH$_2$—CH=CH$_2$
(14) —CH$_2$—CH$_2$—O—CH=CH$_2$
and

(15) 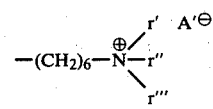

where r′, r″ and r‴, whether identical or different, represent an alkyl radical with 1 to 4 carbon atoms;

or R$_4$ and R$_5$ may represent, together with the nitrogen atom to which they are attached, heterocyclical groupings such as the piperines or morpholines, A and A′, identical or different, represent an anion such as a chloride, bromide, iodide, methylsulphate, acetate, borate, citrate, tartrate, bisulphate, bisulfite, sulphate, or phosphate, and Ac, when p=1, represents a mineral or organic acid, preferably an acid taken from the group made up of hydrochloric acid, hydrobromic acid, nitric acid, acetic acid, butyric acid, and lactic acid;

as well as the copolymers which entail units with the formula (Ia) or (Ib) and, in addition, preferably units with an acrylamide or methacrylamide base or a base from their derivatives, diacetone acrylamide, N-vinyl lactames, vinylic esters, acrylic esters, methacrylic esters, alylicesters, vinylic ethers and α-olefines.

Among the quaternary ammonium polymers of the type defined above, those which are especially preferred or the homopolymer of ammonium diallyl dimethyl chloride, sold under the trade name of MERQUAT 100 and with a molecular weight below 100,000, and the dichloride copolymer of ammonium diallyldimethyl and acrylamide with a molecular weight in excess of 500,000, sold under the trade name of MERQUAT 550 by the MERCK company.

These polymers are described in French Pat. No. 2.080.759 and its certificate of addition No. 2.190.406, as well as in Fench Pat. No. 77.15088 and No. 78.27074, as well as in U.S. Pat. No. 3,862,091. and (B) the quaternary polyammoniums with the formula:

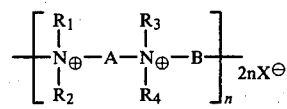

in which R$_1$ and R$_2$, R$_3$ and R$_4$, whether identical or different, represent aliphatic, alicyclic or arylaliphatic radicals containing a maxiumum or 20 carbon atoms or lesser hydroxyaliphatic radicals, or R$_1$ and R$_2$ and R$_3$ and R$_4$, taken together or separately, constitute with the nitrogen atoms to which they are attached heterocucles containing perhaps a second heteroatom other than nitrogen, or R$_1$, R$_2$, R$_3$ and R$_4$ represent a grouping taken from the group made up of:

(i) 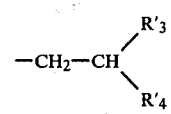

(ii) 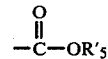

(iii) 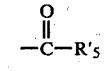

(iv) 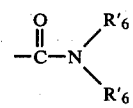

(v) 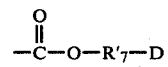

(vi) 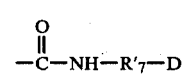

in which

R′$_3$ represents a hydrogen or lesser al alkyl,

R′$_4$ represents —CN,

R′$_5$ represents a lesser alkyl, R′$_6$ represents a hydrogen or a lesser alkyl, R′$_7$ represents an alkene and D represents a quaternary ammonium group;

A and B may represent polymethylenic groups containing from 2 to 20 carbon atems, which may be linear or branched, saturated or unsaturated, and may contain, interspersed in the principal chain, one or several groups with the formula:

(1) 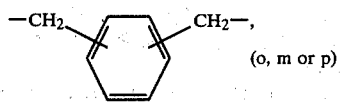

(o, m or p)

(2) —(CH$_2$)$_t$—Y—(CH$_2$)$_t$—
with Y representing O, S, SO, SO$_2$ or a radical with the formula:

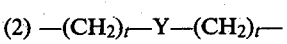

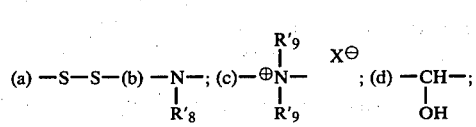

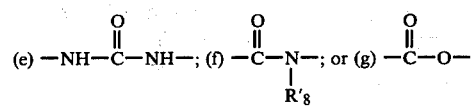

where X$^\ominus$ represents an anion derived from a mineral or organic acid, t is 2 or 3, R′$_8$ represents a hydrogen or lesser alkyl, R′$_9$ represents a lesser alkyl, or A and R$_1$ and R$_3$ form, with the two nitrogen atoms to which they are attached, a piperazine cycle; in addition, if A represents an alkylene or hydroxyalkylene radical, linear or branched, saturated or unsaturated, B may also represent a group: —(CH$_2$)$_{n'}$—CO—D—OC—(CH$_2$)$_{n'}$— in which n' represents a whole number between 1 and 10 and D represents:

(a) a spare glycol with the formula —O—Z—O—, where Z represents a linear or branched hydrocarbon radical or a group with the formula

or

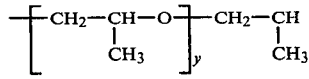

in which x and y represent a whole number from 1 to 4 corresponding to a definite and unique degree of polymerization or any number from 1 to 4 corresponding to an average degree of polymerization;

(b) a spare bi-secondary diamine such as a piperazine derivative with the formula:

(c) a spare bi-primary diamine with the formula:

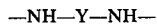

where Y represents a linear or branched hydrocarbon radical or the bivalent radical:

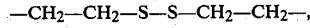

(d) a urylene group with the formula —NH—CO—NH—; $X^{\ominus}$ is an anion such as chloride or bromide, and n is such that the molecular mass is between 1,000 and 100,000.

Polymers of this type are described in particular in French Pat. Nos. 2.320.330 and 2.270.846, French patent application Nos. 76 20261 and 2.336.434, and U.S. Pat. Nos. 2,273,780, 2,375,853, 2,388,614, 2,454,547, 3,206,462, 2,261,002, and 2,271,378, which are incorporated by reference.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020, which are incorporated in the present description by reference.

As polymers which are especially preferred and which meet the above definition, those known under the following trade names may be used:

ONAMER M [poly(dimethyl butenylammonium chloride)-α,ω-Bis(triethanol ammonium chloride)], sold by the ONYX Chemical Co.

MIRAPOL A 15, sold by the Miranol Company and having the following formula:

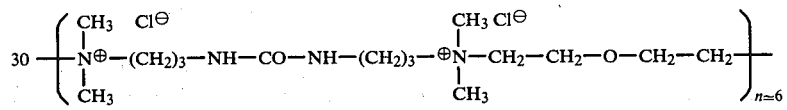

In addition to the reducing agent and the cationic copolymer, the reducing compositions may also contain various ingredients such as, for example, softening agents, inter alia the quaternary ammonium derivatives of lanoline, protein hydrolysates, waxes, agents to make the mixture opaque, perfumes, colorings, nonionic or or cationic tensio-active agents or treating agents.

In the case of a straightening or uncrimping operation, the reducing composition preferably takes the form of a cream, so as to keep the hair as stiff as possible. Such creams are made in the form of "heavy" emulsions, for example using as base a glycerol stearate, glycol stearate, self-emulsionnable waxes, fatty alcohols, etc. Also usable are liquids or gels containing thickening agents such as the carboxyvinylic polymers or copolymers, which "glue" the hair and hold it in the stretched position during the setting time.

The oxidation compositions for the procedure according to the invention contain oxygenated water, an alkaline bromate, a persalt, or a mixture of alkaline bromate and persalt, as an oxidizing agent.

The concentration of oxygenated water may range from 3 to 10 volumes, the concentration of alkaline bromate from 2 to 12 percent, and the persalt concentration from 0.1 to 15 percent by weight with respect to the total weight of the oxidizing composition.

According to the invention, when the oxidizing composition contains the anionic tensio-active agent, the latter is generally present in a concentration ranging between 0.5 and 30 percent, and preferably between 1 and 5 percent, by weight with respect to the total weight of the composition.

In order to prevent any instability phenomena on the part of the anionic tensio-active agent in the oxidizing medium, the oxidizing compositions may be prepared when they are to be used. It should be noted that the anionic tensioactives are to be distinguished from the polyanionic polymers.

Among the different anionic tensio-active agents usable in the oxidizing compositions according to the invention, particular mention may be made of the alkaline salts, ammonium salts, amine salts or amino alcohol salts of the following compounds:

the alkylsulfates, alkylether sulfates, alkylamide sulfates and ether sulfates, alkylarylpolyether sulfates, monoglyceride sulfates, the alkylsulfonates, alkyl amide sulfonates, alkylaryl sulfonates, -olefine sulfonates, the alkyl sulfosuccinates, alkyl ether sulfosuccinates, alkylamide sulfosuccinates, the alkyl sulfosuccinamates, the alkyl sulfoacetates, the alkylpolyglycerol carboxylates, the alkyl phosphates, alkylether phosphates, the alkylsarcosinates, alkylisethionates, alkyl taurates, the alkyl radical of all these compounds being a carbon chain of 12 to 18 atoms of carbon, the fatty acids such as oleic acid, ricinoleic acid, palmitic acid, stearic acid, the acids of oil of copra or hydrogenated oil of copra, carboxylic acids of polyglycolic ethers with the formula:

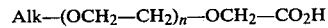

where the substituent Alk corresponds to a chain with 12 to 18 carbon atoms and where n is a whole number between 5 and 15.

Among the anionic tensio-actives, those most particularly preferred are:

the laurylsulfates of sodium, ammonium, or mono-, di- or triethanolamine, the laurylether sulfates of sodium, ammonium, or mono-, di- or triethanolamine, oxyethylenated with the help of 2 to 3 moles of ethylene oxide, the α-olefine sulfonates, the alkylsarcosinates, and the paraffin sulfonates.

The oxidizing compositions may also contain various ingredients, inter alia stabilizing agents, preservatives, softening agents, agents to make the mixture opaque, perfumes, coloring agents, sequestering agents, and acidifying or alkalinizing agents.

When the fixing stage is carried out in two steps, i.e., by the initial application of an oxidizing composition and the subsequent application, perhaps after rinsing, of a composition containing the anionic tensio-active agent, the respective concentrations of the oxidizing agent and anionic tensio-active agent are the same as those indicated above for the compositions using a mixture of the oxidizing agent and anionic tensio-active agent.

However, in the anionic tensio-active solutions, it is possible to use different ingredients, such as, for example, other tensio-active agents or polymers.

The oxidizing compositions used to carry out the procedure according to the invention may also, like the reducing compositions, be of the exothermic type, i.e., those which give off heat when applied, which makes it possible on the one hand to speed up the reconstitution of the bisulfide bonds and, on the other hand, is pleasurable for the person receiving the permanent.

Such compositions for carrying out the oxidation (or fixing) operation are described inter alia in French Pat. No. 2.179.025.

Also the subject of the invention is a complex composition intended for carrying out the procedure according to the invention. This complex composition, made up of the reducing and oxidizing compositions described above and intended to be applied in sequence, is contained in suitable multi-compartment packaging and provided with directions for use.

The following description of several examples of compositions and implementations of the procedure for the permanent shaping of the hair in accordance with the invention is provided for illustration purposes and is in no way restrictive.

EXAMPLE 1

A permanent reshaping of the hair is effected by applying the following reducing composition to the entire head of hair:

| Thioglycolic acid | 8 g |
|---|---|
| Ammonia q.s.p. | pH 7 |
| Ammonium bicarbonate | 6.5 g |
| Sequestering agent | 0.2 g |

Cationic polymer constituted by patterns with the formula:

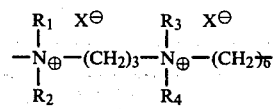

where $R_1$, $R_2$, $R_3$, $R_4$ represent —$CH_3$ and

| X represents Cl (100 percent active material) | 3 g |
|---|---|
| Fatty acid polyoxyethlenated with the help of 20 Moles of ethylene oxide | 1 g |
| Perfume | 0.5 g |
| Water q.s.p. | 100 ml. |

The hair is then rolled on rollers with a diameter ranging from 4 mm to 10 mm, and the composition is allowed to act for 10 to 15 minutes.

After rinsing, the following oxidizing composition is applied to the reduced hair:

| Oxygenated water | 8 volumes |
|---|---|
| Phenacetine | 0.2 g |
| Stabilizer | 0.2 g |
| Phosphoric acid q.s. | pH 4 |
| Alkyl ($C_{12}$-$C_{18}$) ethersulfate of ammonium with 2 Moles of ethylene oxide | 2 g |
| Sequestering agent | 0.2 g |
| Water q.s.p. | 100 ml. |

The composition is allowed to act for 5 minutes, after which the hair is rinsed with water and the rollers are removed.

The hair is soft to the touch and easily combable.

Following the same operational method as described under Example 1 above, permanents were also performed using the following reducing and oxidizing compositions:

EXAMPLE 2

(a) Reducing composition

| Thioglycolic acid | 6 g |
|---|---|
| Ammonia q.s.p. | pH 9.5 |
| Sequestering agent | 0.2 g |
| Cationic polymer as defined in Example 1 | 2 g |
| Protein hydrolysate | 1 g |
| Perfume | 0.5 g |
| Water q.s.p. | 100 ml. |

(b) Oxidizing composition

At the time of use, an oxidizing composition is prepared by mixing 100 ml of part A and 10 ml of part B below:

| Part A | |
|---|---|
| Oxygenated water | 9 volumes |
| Phenacetine | 0.1 g |
| Citric acid | 0.2 g |
| Phenyl alkyl polyoxyethelenate with 9 Moles of ethylene oxide | 1 g |
| Perfume | 0.5 g |
| Water q.s.p. | 100 ml |
| Part B | |
| Ammonium lauryl sulfate (30 percent) | 40 g |
| Sequestering agent | 0.2 g |
| Alkanizing agent q.s | pH 7.5 |
| Preservative | 0.2 g |
| Water q.s.p. | 100 ml. |

Part B above may be replaced by the following:

| Part B' | |
|---|---|
| Sodium lauryl ethersulfate with 2 Moles of ethylene oxide (25 percent) | 50 g |
| Sequestering agent | 0.2 g |
| Alkanizing agent q.s. | pH 7.5 |
| Preservative | 0.2 g |
| Water q.s.p. | 100 ml |

EXAMPLE 3

(a) Reducing composition

| | |
|---|---|
| Thioglycolic acid | 5 g |
| Ammonium bicarbonate | 8.5 g |
| Sequestering agent | 0.2 g |

Cationic polymer made up of patterns having the formula:

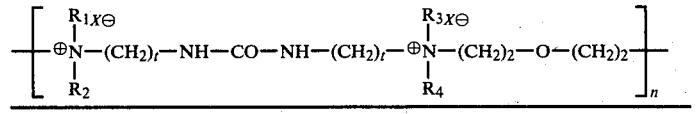

where $R_1$, $R_2$, $R_3$ and $R_4 = CH_3$
$t = 3$
$X = Cl$
$n \simeq 6$ MIRAPOL A 15 (100 percent active material)

| | |
|---|---|
| | 2 g |
| Oleic alcohol polyoxyethylenated with 20 Moles of ethylene oxide | 1 g |
| Perfume | 0.5 g |
| Water q.s.p. | 100 ml |

(b) Oxidizing composition

| | |
|---|---|
| Sodium bromate | 10 g |
| Ammonium lauryl ether sulfate with 2 Moles of ethylene oxide (95 percent) | 2.5 g |
| Preservative | 0.1 g |
| Alkanizing agent q.s. | pH 7.5 |
| Water q.s.p. | 100 ml |

The above oxidizing composition may be replaced by the following composition:

| | |
|---|---|
| Potassium bromate | 9 g |
| Sodium lauryl sulfate (95 percent) | 2 g |
| Preservative | 0.1 g |
| Alkanizing agent q.s. | pH 7.5 |
| Water q.s.p. | 100 ml. |

EXAMPLE 4

A cardboard packate consisting of three compartments, provided with directions for use, contains in separate spaces the following reducing composition and parts A and B of the oxidizing composition:

(a) Reducing composition

| | |
|---|---|
| Ammonium thiolactate | 5 g |
| Monoethanolamine | 1.2 g |
| Sequestering agent | 0.2 g |

Cationic polymer made up of patterns with the formula:

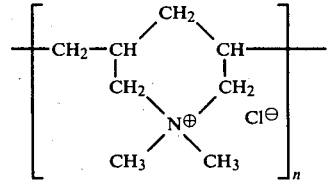

known under the trade name of MERQUAT 100

| | |
|---|---|
| (100 percent active material) | 2 g |
| Oleic alcohol polyoxyethylenated with 20 Moles of ethylene oxide | 1 g |
| Perfume | 0.5 g |
| Water q.s.p. | 100 ml |

(b) Oxidizing composition

At the time of use, an oxidizing composition is prepared by mixing 100 ml of Part A and 10 ml of Part B below:

| Part A | |
|---|---|
| Oxygenated water | 9 volumes |
| Phenacetine | 0.1 g |
| Citric acid | 0.2 g |
| Nonyl phenol polyoxyethylenated with 9 Moles of ethylene oxide | 1 g |
| Perfume | 0.5 g |
| Water q.s.p. | 100 ml |
| Part B | |
| Ammonium lauryl ether sulfate with 2 Moles of ethylene oxide (95 percent) | 15 g |
| Sequestering agent | 0.2 g |
| Alkanizing agent q.s. | pH 7.5 |
| Preservative | 0.2 g |
| Water q.s.p. | 100 ml |

EXAMPLE 5

(a) Reducing composition

| | |
|---|---|
| Ammonium sulfite | 4 g |
| Ammonium bisulfite | 3.3 g |
| Monoethanolamine | 3.9 g |

Cationic polymer made up of patterns with the formula:

-continued

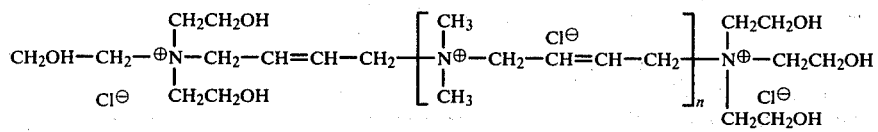

(b) Oxidizing composition

At the time of use, an oxidizing composition is prepared by mixing 100 ml of Part A and 10 ml of Part B below:

| Part A | |
|---|---|
| Oxygenated water | 9 volumes |
| Phenacetine | 0.1 g |
| Citric acid | 0.2 g |
| Nonyl phenol polyoxyethylenated with 9 Moles of ethylene oxide | 1 g |
| Perfume | 0.5 g |
| Water q.s.p. | 100 ml |
| Part B | |
| Sodium lauryl sulfate (95 percent) | 20 g |
| Sequestering agent | 0.2 g |
| Alkanizing agent q.s. | pH 7.5 |
| Preservative | 0.2 g |
| Water q.s.p. | 100 ml. |
| Part B above may be replaced by the following Part B': | |
| Triethanolamine lauryl sulfate (40 percent) | 20 g |
| Sequestering agent | 0.2 g |
| Alkanizing agent q.s. | pH 7.5 |
| Preservative | 0.2 g |
| Water q.s.p. | 100 ml. |

EXAMPLE 6

(a) Reducing composition

A reducing composition is obtained at the time of use by mixing the following parts A and B:

| Part A | |
|---|---|
| Glycerol monothioglycolate (100 percent) | 20 g |
| Glycerine | 10 g |
| Part B | |
| Monoethanolamine q.s.p. (after mixing parts A and B) | pH 7 |
| Cationic polymer as defined in Example 1 | 2 g |
| Nonionic tensio-active (fatty polyethoxy ether alcohols in C12-C14 with 11 Moles of ethylene oxide) | 1 g |
| Perfume | 0.5 g |
| Water q.s.p. | 100 ml |
| (b) Oxidizing composition | |
| Oxygenated water | 8 volumes |
| Phenacetine | 0.2 g |
| Stabilizing agent | 0.2 g |
| Phosphoric acid q.s. | pH 4 |
| Alkyl (C12–C18) ether sulfate of ammonium with 2 Moles of ethylene oxide | 2 g |
| Sequestering agent | 0.2 g |
| Water q.s.p. | 100 ml. |

EXAMPLE 7

A permanent reshaping of the hair is effected by applying a reducing compound resulting from the mixture of the following ingredients to the entire head of hair:

| Thioglycolic acid | 8 g |
|---|---|
| Ammonia q.s.p. | pH 7 |
| Ammonium bicarbonate | 6.5 g |
| Sequestering agent | 0.2 g |
| Cationic polymer as defined in Example 1 | 3 g |
| Oleic alcohol polyoxyethylenated with 20 Moles of ethylene oxide | 1 g |
| Perfume | 0.5 g |
| Water q.s.p. | 100 ml. |

The hair is then rolled on rollers with a diameter of from 7 mm to 15 mm and the composition is allowed to act for a period of about 5 to 15 minutes.

After rinsing, the oxidizing composition resulting from the mixture of the following ingredients is applied to the entire head of hair:

| Oxygenated water | 7 volumes |
|---|---|
| Phenacetine | 0.2 g |
| Stabilizing agent | 0.2 g |
| Phosphoric acid q.s.p. | pH 3 |
| Water q.s.p. | 100 ml. |

After allowing this composition to act for a period of from 5 to 10 minutes, 20 ml of a so-called developing solution with the composition listed below is applied to the hair:

| Lauryl ether sulfate of ammonium with 2 Moles of ethylene oxide (95 percent) | 25 g |
|---|---|
| Preservative | 0.2 g |
| Alkanizing agent q.s. | pH 7 |
| Sequestering agent | 0.2 g |
| Water q.s.p. | 100 ml. |

After allowing this developing solution to act for a few minutes, the hair is rinsed extensively and the rollers are removed.

The hair is soft to the touch and easy to comb.

EXAMPLE 8

A permanent reshaping of the hair is effected by applying to the entire head of hair an exothermic reducing composition obtained by mixing 90 ml of the following part A with 20 ml of the following part B:

| Part A | |
|---|---|
| Thioglycolic acid | 12 g |
| Ammonia q.s.p. | pH 7 |
| Monoethanolamine | 5 g |
| Sequestering agent | 0.2 g |
| Cationic polymer as defined in Example 1 | 2 g |
| Oleic alcohol oxyethylenated with 20 Moles of ethylene oxide | 1 g |
| Perfume | 0.5 g |
| Protein hydrolysate | 1 g |
| Water q.s.p. | 100 ml |
| Part B | |
| Oxygenated water | 15 volumes |
| Stabilizing agent | 0.2 g |
| Phosphoric acid q.s.p. | pH 2.5 |

-continued

| | |
|---|---|
| Water q.s.p. | 100 ml. |

The hair is then rolled on curlers and the composition is allowed to act for a period of about 10 to 15 minutes.

After a water rinse, an oxidizing composition resulting from the mixture of the following ingredients is applied to the entire head of hair:

| | |
|---|---|
| Oxygenated water | 8 volumes |
| Stabilizing agent | 0.2 g |
| Paraffin sulfonate (C14–C16) | 2 g |
| Citric acid q.s.p. | pH 3 |
| Sequestering agent | 0.2 g |
| Water q.s.p. | 100 ml. |

After allowing this composition to act for about 5 minutes, the hair is rinsed in water and the curlers are removed.

The hair is soft to the touch and easy to comb.

EXAMPLE 9

According to the same operational procedure described under Example 8, the first step of a permanent is carried out using the same exothermic reducing composition.

However, after the rinsing, an oxidizing composition, also exothermic, was applied to the hair after preparing same at the time of use by mixing 100 g of part A and 20 g of part B below:

| | |
|---|---|
| Part A | |
| Oxygenated water | 11 volumes |
| Stabilizing agent | 0.2 g |
| Phosphoric acid q.s.p. | pH 4 |
| Ammonium lauryl sulfate | 2 g |
| Sequestering agent | 0.2 g |
| Perfume | 0.5 g |
| Water q.s.p. | 100 ml |
| Part B | |
| Sodium sulfate | 12 g |
| Water q.s.p. | 100 g. |

After allowing the foregoing to act for a period of 5 to 10 minutes, the curlers are removed and the hair freely rinsed. An excellent quality permanent is obtained.

EXAMPLE 10

A reducing composition was prepared with the following formula:

| | |
|---|---|
| Thioglycolic acid | 7 g |
| Ammonia | 6.5 g |
| Ammonium bicarbonate | 6 g |
| Sequestering agent | 0.2 g |
| Cationic polymer* | 1 g |
| Cationic polymer known under the trade name of ONAMER M (100 percent active materials) | 1 g |
| Ethoxylated fatty alcohol (20 Moles ethylene oxide) | 1 g |
| Perfume | 0.5 g |
| Water q.s.p. | 100 ml |

*This cationic polymer is the one used in Example 1 above.

This reducing composition may be used im place of the one in Example 1 in the procedure according to the invention.

EXAMPLE 11

An exothermic reducing composition is obtained by mixing, at the time of use, 50 g of part A and 70 g of part B below:

| | |
|---|---|
| Part A | |
| Glycerol monothiovglycolate (100 percent) | 75 g |
| Glycerine | 25 g |
| Part B | |
| Sodium bromate | 2.5 g |
| Cationic polymer* | 2 g |
| Monoethanolamine q.s.p. | pH 11 |
| Polyoxyethylenated oleic alcohol (with 20 Moles of ethylene oxide) | 1 g |
| Perfume | 0.5 g |
| Water q.s.p. | 100 ml |

*This cationic polymer is the one used in Example 1.

The exothermic reducing composition obtained may be used in place of the one described in Example 8.

EXAMPLE 12

A permanent reshaping of the hair is effected by applying, to the entire head of hair, a reducing composition resulting from mixture at the time of use of:

7 g of cystein chlorhydrate to 100 ml of the following solution:

| | |
|---|---|
| Urea | 5 g |
| Monoethanolamine | 6.5 g |
| Diethanolamine | 6.5 g |
| Cationic polymer* | 3 g |
| Oleic alcohol polyoxyethylenated with 20 Moles of ethylene oxide | 1 g |
| Perfume | 0.3 g |
| Water q.s.p. | 100 ml |

*Same cationic polymer as in Example 1.

After rolling of the hair, the reducing composition prepared as described is allowed to act for a period of time generally ranging from 20 to 30 minutes depending on the nature of the hair, preferably using a preheated hood.

After rinsing, next applied to the entire head of hair is an oxidizing composition such as the ones described in Examples 1 to 9.

EXAMPLE 13

| | |
|---|---|
| A. A reducing composition was prepared with the following formula: | |
| Sodium bisulfite | 7 g |
| Thioglycolic acid | 1.5 g |
| Monoethanolamine | 3.5 g |
| Diethanolamine | 3 g |
| Cystein chlorhydrate | 1 g |
| Cationic polymer* | 1.5 g |
| Ethoxylated fatty alcohol (20 Moles ethylene oxide) | 1 g |
| Perfume | 0.3 g |
| Water q.s.p. | 100 ml |
| B. A reducing composition was prepared with the following formula: | |
| Sodium metabisulfite | 4 g |
| Ammonium sulfite | 3.5 g |
| Monoethanolamine | 2 g |
| Diethanolamine | 2 g |
| Borax | 2 g |
| Cystein chlorhydrate | 1.5 g |
| Cationic polymer* | 2 g |
| Oxyethylenated fatty alcohol (20 Moles ethylene oxide) | 1 g |

-continued

| | |
|---|---|
| Perfume | 0.3 g |
| Water q.s.p. | 100 ml |

*The cationic polymer is the same as in Example 1.

Reducing compositions A and B are used in the first step of the permanent according to the invention, their application being followed by the application of an oxidizing composition such as those described in Examples 1 to 9.

EXAMPLE 14

Hair straightening is carried out by applying the following reducing composition to the entire head of hair:

| A. Reducing composition | |
|---|---|
| Nonionic autoemulsionnable wax | 8 g |
| Thioglycolic acid | 8 g |
| Ammonia (20 percent) | 16 g |
| Sequestering agent | 0.2 g |
| Cationic polymer (100 percent active materials) | 1.5 g |
| Perfume | 0.3 g |
| Water q.s.p. | 100 g. |

The cationic polymer has patterns with the formula:

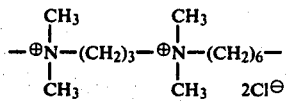

This composition is applied, and the hair is then smoothed by hand or with a comb.

After a setting period (generally lasting from 15 to about 30 minutes depending on the type of hair), the hair is freely rinsed in warm water, after which neutralization (or fixing) using the following oxidizing composition:

| B. Oxidizing composition | |
|---|---|
| Oxygenated water | 6 volumes |
| Stabilizing agents | 0.2 g |
| Citric acid | 0.2 g |
| Ammonium lauryl sulfate | 2 g |
| Water q.s.p. | 100 ml. |

The reducing and oxidating compositions were separately contained in a two-compartment cardboard package provided with directions for use.

The stabilizing agents may be selected principally from phenacetine, sodium pyrophosphate, sodium stannate and the sulfate of hydroxyquinolein.

EXAMPLE 15

In like manner, a straightening operation was carried out using the following compositions:

| A. Reducing composition | |
|---|---|
| Partially oxyethylenated stearylic cetyl alcohol (30 Moles ethylene oxide) | 10 g |
| Thiolactic acid | 7 g |
| Ammonia (20 percent) | 6 g |
| Triethanolamine | 7 g |
| Sequestering agent | 0.2 g |
| Cationic polymer known under the trade name of Merquat 100 (100 percent active materials) | 2 g |
| Perfume | 0.2 g |
| Water q.s.p. | 100 g. |

| B. Oxidizing composition | |
|---|---|
| Oxygenated water | 6 volumes |
| Stabilizing agents | 0.2 g |
| Paraffin sulfonate ($C_{14}$-$C_{16}$) | 2 g |
| Citric acid q.s.p. | pH 4 |
| Sequestering agent | 0.2 g |
| Water q.s.p. | 100 ml. |

The Merquat 100 cationic polymer is made up of patterns with the formula:

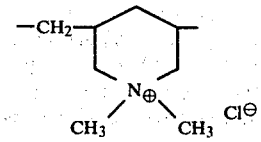

We claim:

1. Procedure for the permanent reshaping of hair consisting in a first step involving reduction of the bisulfide bonds of the keratin by applying a reducing composition, then in a second step for reforming the said bonds by applying an oxidizing composition, characterized by the fact that the reduction stage is carried out using a reducing composition containing at least one cationic polymer and the fact that the fixing stage is carried out in the presence of at least one anionic tensio-active agent.

2. Procedure according to claim 1, characterized by the fact that the said reducing composition is allowed to act for a period of time ranging from 5 to 30 minutes.

3. Procedure according to claim 1, characterized by the fact that the said oxidizing composition is allowed to act for a period of time ranging from 2 to 10 minutes.

4. Procedure according to any one of the above claims, characterized by the fact that the fixing stage is carried out using an oxidizing compound containing the anionic tensio-active agent.

5. Procedure according to any one of claims 1 to 3, characterized by the fact that the fixing stage is carried out in two steps, the first step consisting in the application of an oxidizing composition and the second step in the application of a composition containing the anionic tensio-active agent.

6. Procedure according to any one of claims 1 to 6, characterized by the fact that the cationic polymer is present in the reducing compound in a concentration of between 0.2 percent and 5 percent by weight with respect to the total weight of the said composition.

7. Procedure according to any one of claim 1 to 6, characterized by the fact that the pH of the reducing composition is between 6.5 and 10.

8. Procedure according to claim 4, characterized by the fact that the oxidizing composition contains the anionic tensio-active agent in a concentration of between 0.5 and 30 percent by weight with respect to the total weight of the said composition.

9. Procedure according to any one of the preceding claims, characterized by the fact that the anionic tensio-active agent is preferably a lauryl sulfate of sodium, ammonium, or mono-, di- or triethanolamine, a lauryl ether sulfate of sodium, ammonium, or mono-, d-, or triethanolamine oxyethylenated using 2 to 3 moles of ethylene oxide, an -olefin sulfonate, an alkylsarcosinate or a paraffin sulfonate.

10. Two-part composition intended for successive use in carrying out the procedure according to any one of claims 1 to 9, characterized by the fact that the first part consists in a reducing composition containing at least one cationic polymer and the second part consists in an oxidizing composition containing at least one anionic tensio-active agent.

11. Composition according to claim 10, characterized by the fact that the said first part is itself in two parts, one of which consists in the reducing composition and the other in a composition containing the cationic polymer, said two parts being designed to be mixed at the time of use.

12. Composition according to claim 10, characterized by the fact that the said second part is itself in two parts, one consisting in the oxidizing composition and the other in a composition containing the anionic tensio-active agent, the said two parts being designed to be mixed at the time of use or to be applied to the hair in succession.

13. Composition according to any one of claims 10 and 11, characterized by the fact that the first part made up of the reducing composition, whether or not it contains the polymer in mixture, also contains cosmetic ingredients such as softening agents, thickening agents, protein hydrolysates, waxes, agents to make the mixture opaque, perfumes, coloring agents, nonionic or cationic tensio-actives, or treating agents.

14. Composition according to any one of claims 10 and 12, characterized by the fact that the second part made up of the oxidizing composition, whether or not it contains the anionic tensio-active agent in mixture, also contains cosmetic ingredients such as stabilizing agents, preservatives, softening agents, agents to make the mixture opaque, perfumes, coloring agents, sequestering agents, acidifying agents, or alkalizing agents.

* * * * *